US011857784B2

(12) United States Patent
Ryotokuji (10) Patent No.: US 11,857,784 B2
(45) Date of Patent: Jan. 2, 2024

(54) METHOD FOR CONDUCTING STIMULUS TREATMENT

(71) Applicant: Kenji Ryotokuji, Chiba (JP)

(72) Inventor: Kenji Ryotokuji, Chiba (JP)

( * ) Notice: Subject to any disclaimer, the term of this patent is extended or adjusted under 35 U.S.C. 154(b) by 1375 days.

(21) Appl. No.: 16/261,121

(22) Filed: Jan. 29, 2019

(65) Prior Publication Data

US 2019/0151139 A1    May 23, 2019

Related U.S. Application Data

(63) Continuation of application No. 15/161,631, filed on May 23, 2016, now abandoned, which is a
(Continued)

(30) Foreign Application Priority Data

Feb. 24, 2012    (JP) .................................. 2012-038386

(51) Int. Cl.
*A61F 7/00*    (2006.01)
*A61N 1/36*    (2006.01)
(Continued)

(52) U.S. Cl.
CPC ......... *A61N 1/36031* (2017.08); *G16H 40/20* (2018.01); *A61B 8/06* (2013.01);
(Continued)

(58) Field of Classification Search
CPC ... G16H 40/20; A61B 8/06; A61F 2007/0093; A61F 2007/0295; A61F 7/007;
(Continued)

(56) References Cited

U.S. PATENT DOCUMENTS

2005/0222486 A1*  10/2005  Shin ................. A61N 2/004
                                                600/506
2011/0034782 A1*  2/2011  Sugimachi ............ A61H 39/04
                                                601/1

FOREIGN PATENT DOCUMENTS

JP    2001-112843 A    4/2001
JP    2008-113876 A    5/2008
(Continued)

OTHER PUBLICATIONS

Erasala GN, et al., "The Effect of Tropical Heat Treatment on Trapezius Muscle Blood Flow using Power Doppler Ultrasound", Physical Therapy, 2001; Abstract. (2 pages). Office Action dated Oct. 10, 2017 issued in U.S. Appl. No. 14/379,850.
(Continued)

*Primary Examiner* — Tigist S Demie
(74) *Attorney, Agent, or Firm* — WHDA, LLP (57) ABSTRACT

A method of conducting a stimulus treatment includes the steps of examining health conditions of a subject to obtain examination data information of the subject, registering the examination data information in an information accumulation device, planning a schedule of the stimulus treatment determined to be suitable for the subject based on the examination data, and conducting the stimulation application treatment by applying a stimulation to a stimulation receiving site of the subject with a stimulation application device so as to increase the blood flow in the subject by 60% or more after the application of stimulation, as compared to the blood flow before the application of the stimulation.

10 Claims, 8 Drawing Sheets

Related U.S. Application Data continuation-in-part of application No. 14/379,850, filed as application No. PCT/JP2012/076056 on Oct. 1, 2012, now abandoned.

(51) Int. Cl.

| | | |
|---|---|---|
| *G16H 40/20* | (2018.01) | |
| *A61H 39/00* | (2006.01) | |
| *A61H 39/06* | (2006.01) | |
| *A61F 7/02* | (2006.01) | |
| *A61B 8/06* | (2006.01) | |
| *A61H 39/08* | (2006.01) | |

(52) U.S. Cl.
CPC ....... *A61F 7/007* (2013.01); *A61F 2007/0093* (2013.01); *A61F 2007/0295* (2013.01); *A61H 39/002* (2013.01); *A61H 39/06* (2013.01); *A61H 39/08* (2013.01); *A61H 2201/0207* (2013.01); *A61H 2201/168* (2013.01); *A61H 2201/5005* (2013.01); *A61H 2201/5023* (2013.01); *A61H 2201/5038* (2013.01); *A61H 2230/25* (2013.01); *A61H 2230/505* (2013.01)

(58) Field of Classification Search
CPC ...... A61H 2201/0207; A61H 2201/168; A61H 2201/5005; A61H 2201/5023; A61H 2201/5038; A61H 2230/25; A61H 2230/505; A61H 39/002; A61H 39/06; A61H 39/08; A61N 1/36031

See application file for complete search history.

(56) References Cited

FOREIGN PATENT DOCUMENTS

| JP | 2010-046515 A | 3/2010 |
|---|---|---|
| JP | 2012-005595 A | 1/2012 |
| WO | 2007/047152 A2 | 4/2007 |

OTHER PUBLICATIONS

International Search Report dated Jan. 8, 2013, issued in corresponding application No. PCT/JP2012/076056.

Hull, Heat-Enhanced Transdermal Drug Delivery: A survey Paper, http://jrnlappliedresearch.com/articles/Vol2Iss1/Hull.htm, Apr. 2002, pp. 1-5; Office Action dated Jul. 29, 2016, issued in U.S. Appl. No. 14/379,850.

Horbal, The benefits of Orthotics for a patient with metatarsalgia, CRAJ vol. 19, No. 2, 2009, pp. 4-8; Office Action dated Jul. 29, 2016, issued in U.S. Appl. No. 14/379,850.

\* cited by examiner

Blood flow

Symptom;Excess Stress

| Doppler | 5-Jun | 9-Jun |
|---|---|---|
| at rest 5 minutes | 8.1196 | 2.1966 |
| During Stimulation | 10.9277 | 4.6551 |
| End of Stimulation 1 minute agc | 13.8514 | 2.2526 |
| After Completion of Stimulation | 14.791 | 3.0983 |
| iInclease Rate of Blood Flow | 1.82164146 | 1.410498042 |

Symptom;Cardiac Failture

| Doppler | 7-Jul | 10-Jul |
|---|---|---|
| at rest 5 minutes | 1.2446 | 2.0953 |
| During Stimulation | 4.8361 | 4.1657 |
| End of Stimulation 1 minute agc | 4.5834 | 3.1638 |
| After Completion of Stimulation | 4.6877 | 3.5302 |
| iInclease Rate of Blood Flow | 3.766430982 | 1.684818403 |

Symptom;Weak Constitution

| Doppler | 9-Jul | 12-Jul |
|---|---|---|
| at rest 5 minutes | 0.7093 | 1.1584 |
| During Stimulation | 1.317 | 2.8652 |
| End of Stimulation 1 minute agc | 0.929 | 2.8459 |
| After Completion of Stimulation | 1.2221 | 3.3652 |
| iInclease Rate of Blood Flow | 1.72298805 | 2.910065721 |

FIG.4

| Patient | stimulation before | stimulation after | increase rate |
|---|---|---|---|
| No.1 | 1.287 | 2.1036 | 63 |
| No.2 | 3.2791 | 8.0098 | 144 |
| No.3 | 1.7603 | 2.959 | 68 |
| No.4 | 2.8101 | 4.6872 | 68 |
| No.5 | 5.9857 | 13.0065 | 117 |
| No.6 | 3.453 | 6.9631 | 102 |
| No.7 | 2.0954 | 4.7401 | 126 |
| No.8 | 1.4332 | 3.5227 | 146 |
| No.9 | 1.0091 | 1.7377 | 72 |
| No.10 | 3.9592 | 8.0699 | 104 |
| No.11 | 1.5635 | 3.8743 | 148 |

METHOD FOR CONDUCTING STIMULUS TREATMENT

CROSS-REFERENCE OF RELATED APPLICATIONS

This application is a Divisional of copending U.S. patent application Ser. No. 15/161,631, filed on May 23, 2016, which is a Continuation-In-Part of U.S. patent application Ser. No. 14/379,850, filed on Dec. 29, 2014, which is a U.S. National Stage Entry of International Application No. PCT/JP2012/076056, filed Oct. 1, 2012, which claims priority of Japanese Patent Application No. 2012-038386, filed on Feb. 24, 2012, the entire contents of which are incorporated herein by reference.

TECHNICAL FIELD

The present invention relates to a method and system for conducting stimulus treatments to be performed in a stimulation treatment institution, which may be performed with a thermal stimulus treatment and/or transmission evaluation method and/or a method for evaluating drug benefits by thermal stimulus transmission for evaluating improvements in psychological stress, etc., by supplying thermal stimulus to a specific site with an electrical thermal stimulus apparatus.

BACKGROUND ART

As prior art, Patent Literature 1 is known. Patent Literature 1 states that a thermal stimulus may be easily, accurately as well as objectively evaluated by measuring impedance locus of the skin of an acupuncture patient during acupuncture and inspecting the variation thereof with respect to time. However, there is no description on how the thermal stimulus on medical conditions may be objectively evaluated.

CITATION LIST

PTL 1 Japanese Unexamined Patent Application Publication No. 2001-112843

SUMMARY OF INVENTION

Technical Problem

An object of the present invention is to provide a thermal stimulus evaluation method in which the thermal stimulus on medical conditions can be objectively evaluated. According to the present invention, the increase rate of thermal stimulus which are effective on medical conditions are provided in a database. The increase rate of blood flow which is previously effective on a medical condition accumulated in the database is compared with the increase rate of blood flow measured before and after the application of thermal stimulus to a specific site. The drug supplied in a body may be evaluated by using the increase rate of blood flow.

Solution to Problem

In a thermal stimulus evaluation method to evaluate the thermal stimulus applied to a specific site on a skin surface, the thermal stimulus evaluation method comprises;
  step for measuring a blood flow with a laser Doppler tissue blood flowmeter mounted at the center of an inside wrist joint, before and after the application of thermal stimulus to a specific site that is selected for the application of thermal stimulus;
  step for comparing the increase rate of blood flow before and after the application of thermal stimulus with the increase rate in the database storing the increase rate of blood flow which is previously effective on a medical condition, when the increase rate of blood flow by application of the thermal stimulus at a selected specific site reaches the increase rate of blood flow which is previously effective on a medical condition, the effect of thermal stimulus is recognized, wherein the increase rate of blood flow which is previously effective on a medical condition is 30% or more, preferably 100% or more.

In a thermal stimulus evaluation method to evaluate the thermal stimulus applied to a specific site on a skin surface, the thermal stimulus evaluation method comprises;
  a step for measuring a blood flow with a laser Doppler tissue blood flowmeter mounted at the center of an inside wrist joint, before and after the application of thermal stimulus to a specific site that is selected for the application of thermal stimulus;
  a step for comparing the increase rate of blood flow before and after the application of thermal stimulus with the increase rate in the database storing the increase rate of blood flow which is previously effective on a medical condition; and
  when the increase rate of blood flow by application of the thermal stimulus at a selected specific site not reaches the increasing rate of blood flow which is previously effective on a medical condition, the effect of thermal stimulus is not recognized, in this case, the application of the thermal stimulus is carried out by varying at least one of a thermal stimulus temperature, thermal stimulus time period, a thermal stimulus application method, a pattern of thermal stimulus and a thermal stimulus method, wherein the increase rate of blood flow which is previously effective on a medical condition is 30% or more, preferably 100% or more.

In the thermal stimulus evaluation method, wherein the drug is supplied into a body, and at the time of supplying of the drug, the increase rate of blood flow by application of the thermal stimulus at a selected specific site is preferred to reach the increase rate of blood flow which is previously effective on a medical condition.

In the thermal stimulus evaluation method, the specific site is at least one site of (1) a site between the first and the second metatarsal heads of right and left soles, (2) a site between the second and the third metatarsal heads and (3) a site where an extended line of inner periphery between the first and second and a perpendicular line of an inner ankle crosses.

Advantageous Effects of Invention

According to the present invention, the increase rate of thermal stimulus which are effective on medical conditions are provided in a database. And the increase rate of blood flow before and after applying stimulus to a specific site is compared with the increase rate in the database storing the rate of increase which is previously effective on a medical condition. And when the increase rate of blood flow by application of the thermal stimulus at a selected specific site reaches nearly the same as or higher than the increase rate of blood flow the increase rate of blood rate flow which is previously effective on a medical condition, the effect of thermal stimulus is recognized. Wherein, the increase rate of blood flow which is effective on a medical condition is 30% or more, preferably 100% or more.

And, after the increase rate of blood flow by application of the thermal stimulus at a selected specific site reaches is nearly the same as or higher than the increase rate of blood flow which is previously effective on a medical condition, the drug is supplied into a body.

DESCRIPTION OF EMBODIMENTS

The present invention relates to a thermal stimulus transmission evaluation method and a method for evaluating drug benefits by thermal stimulus transmission for evaluating thermal stimulus applied to a specific site on a skin surface by controlling an electrical thermal stimulus apparatus so as to treat medical conditions such as psychological stress.

A thermal stimulus evaluation method to evaluate the thermal stimulus applied to a specific site on a skin surface is carried by controlling an electrical thermal stimulus controller so as to treat medical conditions such as psychological stress.

The thermal stimulus evaluation method comprises as follows;

A blood flow with a laser Doppler tissue blood flowmeter mounted at the center of an inside wrist joint, before and after the application of thermal stimulus to a specific site that is selected for the application of thermal stimulus is measured.

The increase rate of the blood flow before and after the application of thermal stimulus is obtained. The increase rate of blood flow before and after the application of thermal stimulus step is compared with the increase rate in the database storing the increase rate of blood flow which is previously effective on a medical condition, And when the increase rate of blood flow by application of the thermal stimulus at a selected specific site reaches is nearly the same as or higher than the increase rate blood flow which is previously effective on a medical condition, the effect of thermal stimulus is recognized, and the increase rate of blood flow is effective on a medical condition is 30% or more, preferably 100% or more. And, after the increase rate of blood flow by application of the thermal stimulus at a selected specific site reaches is nearly the same as or higher than the increase rate of blood flow which is previously effective on a medical condition, the drug is supplied into a body.

The thermal stimulus transmission evaluation method includes the following steps.

(1) Step of Examining Medical Conditions such as Psychological Stress

Examination categories of examining medical conditions such as psychological stress include blood pressure, a deep body temperature, salivary amylase and a heart rate (arterial age) immediately before stimulus application after a subject is kept quiet in a face-up position for twenty minutes in consideration of the effect on psychological stress through an autonomic nerve.

(2) Step of Selecting at a Specific Site for Application of the Thermal Stimulus.

The specific site comprises at least one part of os metatarsale primam 1 and 2 interosseous, part os metatarsale primam 2 and 3 interosseous, and part that intersects the perpendicular line of the medial malleolus on an extension line of the medial margin on os metatarsale primam 1 and 2 in foot sole of right and left.

(3) A blood flow is measured with a laser Doppler tissue blood flowmeter mounted at the center of an inside wrist joint, before and after the application of thermal stimulus to a specific site. And the rate of increase of blood flow applying stimulus to a specific site is obtained before and after the application of thermal stimulus. And the increase rate before and after the application of stimulus is compared with the increase rate in the database storing the rate of increase which is previously effective on a medical condition.

Figure 1:
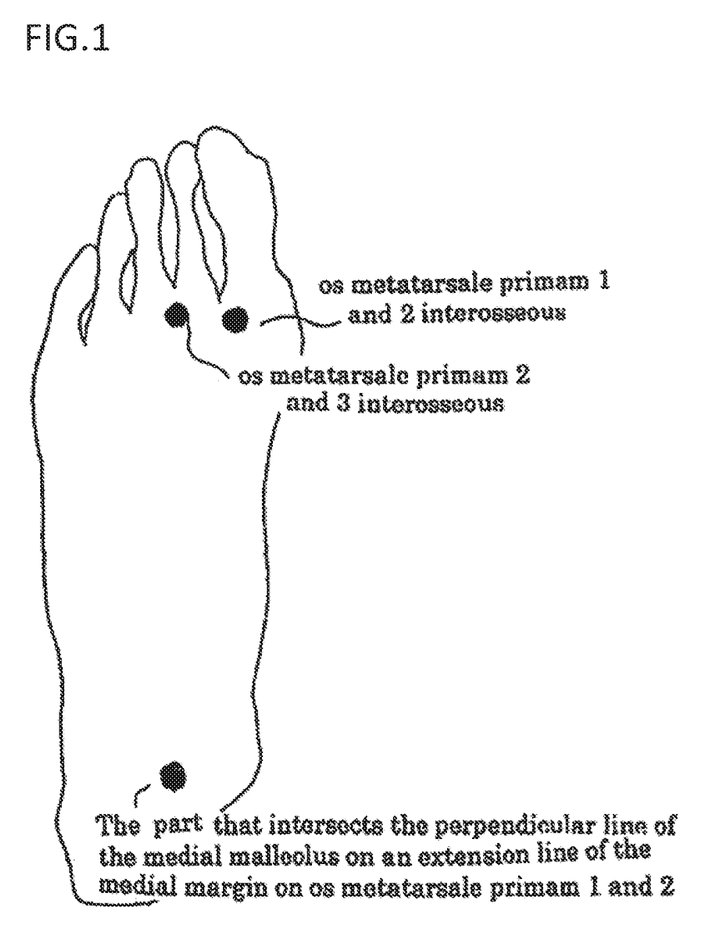
FIG. 1 is a schematic view of a thermal stimulus applied site at sole.
Figure 2:
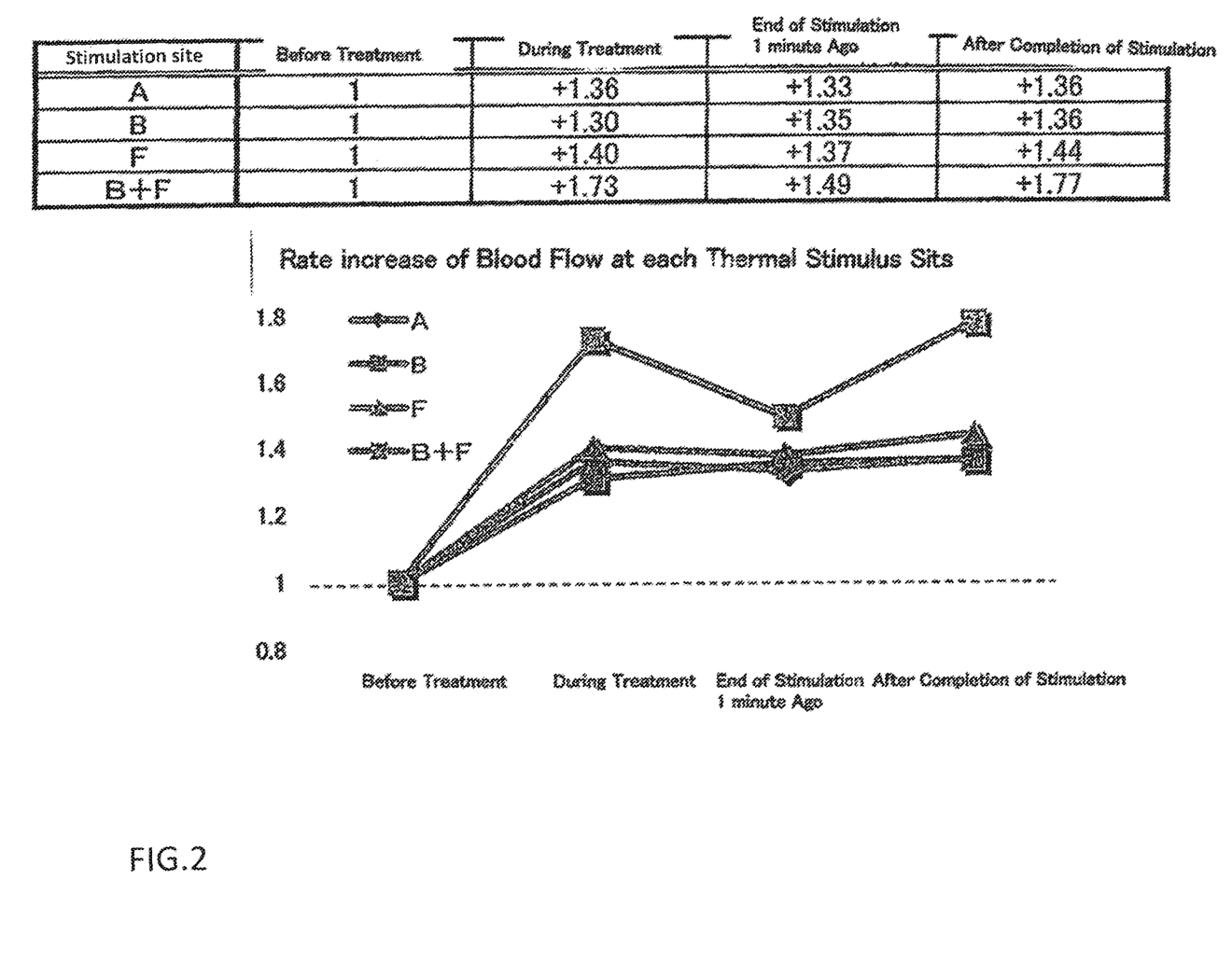
FIG. 2 is a database showing a change rate of blood flow on a specific site.
Figure 3:
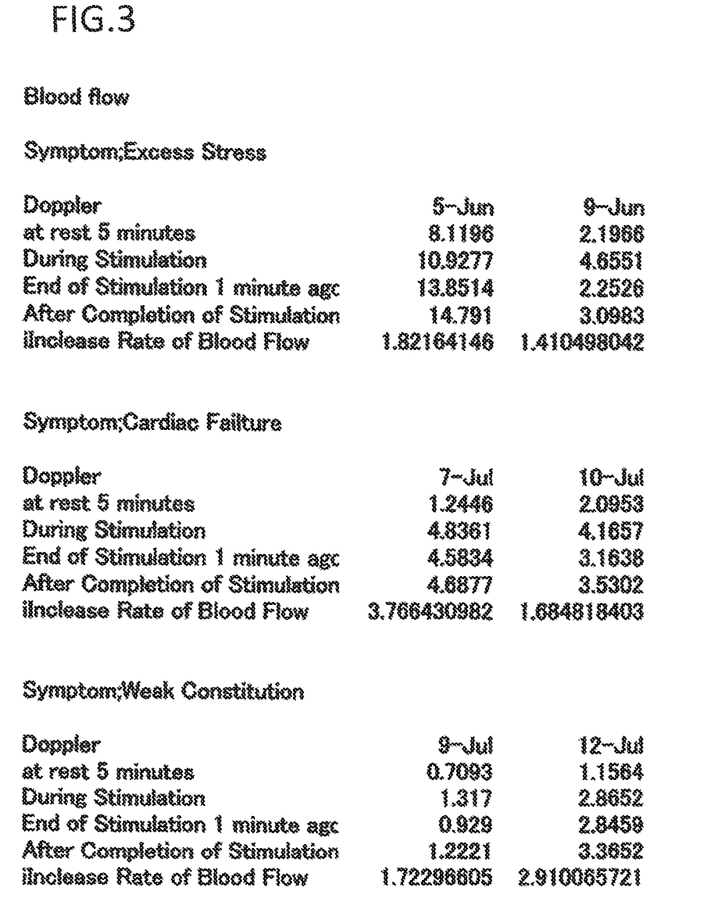
FIG. 3 is a database showing a change rate of blood flow on medical conditions.
Figure 4:
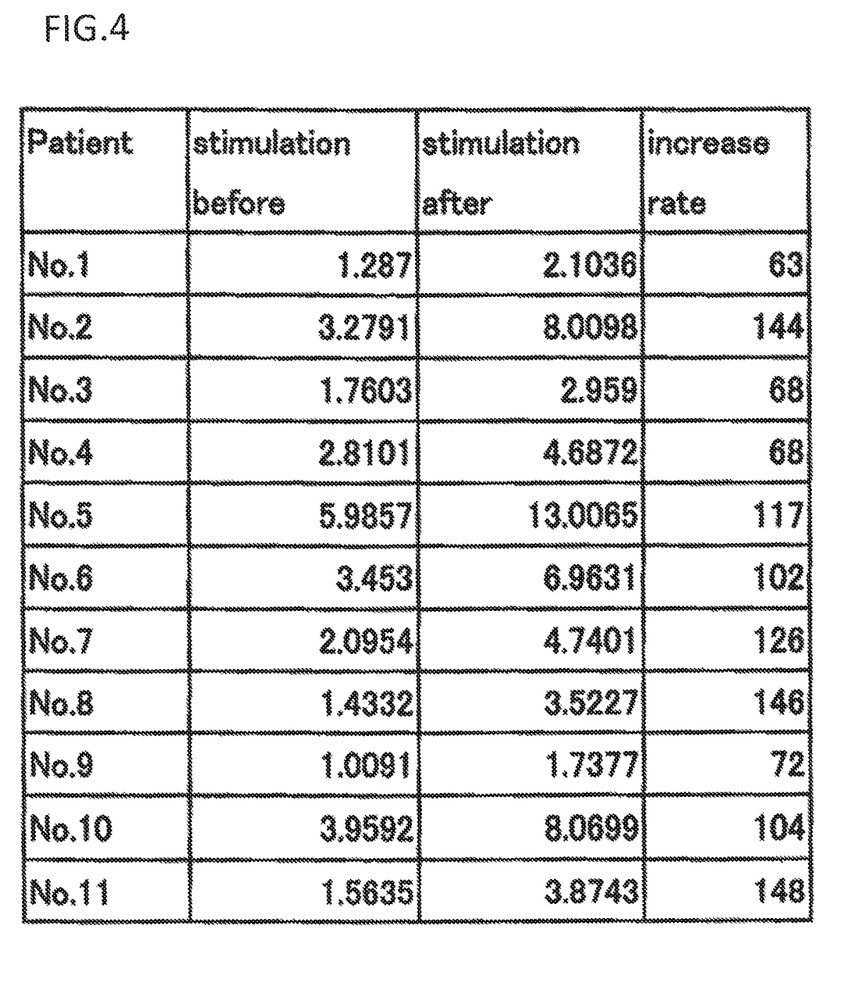
FIG. 4 is a database showing a rate of increase in 11 patients.

FIG. 2-4 shows the database the rate of increase of the blood flow which is previously effective on a medical condition. FIG. 2 shows the rate increase of the blood flow in the thermal stimulus sites in FIG. 1. In the table, (A) is os metatarsale primam 1 and 2 interosseous, (B) is part os metatarsale primam 2 and 3 interosseous, and (F) is part that intersects the perpendicular line of the medial malleolus on an extension line of the medial margin on os metatarsale primam 1 and 2. The favorable combination is (A) and (F). The rate increase in A is +1.30 or more, the rate increase in B is +1.30 or more, the rate increase in F is +1.30 or more and the rate increase in B+F is +1.40 or more.

FIG. 3 is a database indicating the increase rate of blood flow in medical conditions. As for the examples of medical conditions, the increase rate of blood flow in excess stress, cardiac failure and weak constitutions are shown. It is found that the increase rate of blood flow for excess stress is +1.4 or more, the increase rate of blood flow for cardiac failure is +1.6 or more, and the increase rate of blood flow for weak constitutions is +1.7 or more.

FIG. 4 is a database indicating the increase rate of blood flow of eleven patients. The effects were recognized with the increase rate of blood flow of +1.6 or more.

The increase rate of blood flow at the measurement before and after the application of thermal stimulus to a specific site are compared with the increase rate of blood flow in a database, which is provided with the increase rate of blood flow recognized as effective on medical conditions. And the thermal stimulus is evaluated based on the increase rate of blood flow.

It is desirable to measure the volume of blood flow by the laser Doppler tissue rheometer which is attached to an inner and central part of a wrist joint. In a laser tissue blood flowmeter ALF21D (manufactured by ADOVANS), when a living tissue is irradiated with semiconductor laser light (whose wavelength is 780 nm), light reflected from the tissue is converted into an electric signal and the electric signal is processed, thereby obtaining the blood flow information. A C type laser probe (10 mm in diameter, 3 mm in thickness, 2 mm 2 in a laser irradiation area, and 1 mm in measurement depth) of the laser tissue blood flowmeter ALF21D was attached to a central part of a wrist joint horizontal line of a healthy adult, and change of the blood flow was measured, taking a 15-minute rest after a stimulus.

(4) An electrical thermal stimulus controller controls the increase rate of blood flow before and after the application of stimulus. It is preferable that an electrical thermal stimulus controller that is built into an electrical thermal stimulator is driven so as to vary at least one of a thermal stimulus temperature, thermal stimulus time period, a thermal stimulus application method, a pattern of thermal stimulus and a condition of thermal stimulus.

(5) The increase rate of blood flow before and after thermal stimulus application is compared with the increase rate in a database storing the increase rate which is previously effective on medical conditions. The thermal stimulus is evaluated based on the increase rate of blood flow.

Based on the difference of the increase rate between the increase rate of blood flow before and after thermal stimulus application and the increase rate which is previously effective on a medical condition, the effect of thermal stimulus by the application of thermal stimulus is determined. When the increase rate of blood flow by the application of stimulus reaches the increase rate which is previously effective on a medical condition, the effect of the application of thermal stimulus is recognized.

When the increase rate by application of thermal stimulus not reaches the increase rate which are previously effective on medical conditions, it is preferable that the electrical thermal stimulus controller is driven so as to vary at least one of a thermal stimulus temperature, thermal stimulus time period, a thermal stimulus application method, a pattern of thermal stimulus and a condition of thermal stimulus.

Again, the increase rate of blood flow by the application of thermal stimulus to the site is compared the increase rate which is previously effective on a medical condition in the database When the increase rate of blood flow by the application of stimulus reaches the increase rate which is previously effective on a medical condition, the effect of the application of thermal stimulus is recognized.

The method for evaluating drug benefits by thermal stimulus transmission comprises as follows;

A laser Doppler tissue blood flowmeter mounted at the center of an inside wrist joint is provided to measure blood flow. A blood flow before and after the application of thermal stimulus to a specific site that is selected for the application of thermal stimulus is measured with a laser Doppler tissue blood flowmeter mounted at the center of an inside wrist joint.

The increase rate of blood flow measured before and after the application of thermal stimulus to a specific site is compared with the increase rate of blood flow in the database storing blood flow which is previously effective on medical conditions.

The drug is supplied in the body. And at the time of supplying of the drug, the increase rate of blood flow by application of the thermal stimulus at a selected specific site is preferred to reach the increase rate of blood flow which is previously effective on a medical condition.

On the other hand, when the increase rate of blood flow before and after application of the thermal stimulus at a selected specific site not reaches the increase rate of blood flow which is previously effective on a medical condition, the effect by the supplying the drug is not recognized. In this case, the thermal stimulus at a selected specific site is applied by changing the thermal stimulus conditions. And when the increase rate of blood flow before and after application of the thermal stimulus at a selected specific site reaches the increase rate of blood flow which is previously effective on a medical condition, the effect of thermal stimulus is recognized, and the effect by the supplying the drug is recognized. Wherein the drug may be supplied by changing the dose amount and/or an alternate drug.

The sites of the thermal stimulus applied a body surface comprises at least two of part of os metatarsale primam 1 and 2 interosseous, part os metatarsale primam 2 and 3 interosseous, and part that intersects the perpendicular line of the medial malleolus on an extension line of the medial margin on os metatarsale primam 1 and 2 in foot sole of right and left.

(6) "Tanden" breathing method may be further performed in the thermal stimulus evaluation.

The "Tanden" is located at about one fist length down from the navel. In the Tanden breathing method, breathing is performed slowly while bulging out our abdomen. As the diaphragm lowers and the thorax expands further, large breaths can be taken. With this large breathing, attention is paid on inhaling and exhaling breaths with a long interval in-between to empty mind (mindlessness). Accordingly, autonomic nerve which is disturbed by stress can be adjusted.

Figure 5:
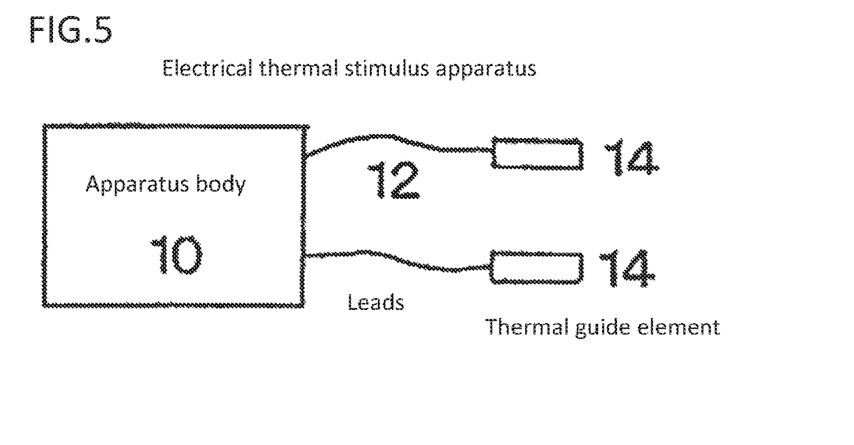
FIG. 5 is a schematic view of an electrical thermal stimulus apparatus according to the invention.

FIG. 5 a schematic view of an electrical thermal stimulus apparatus according to the present invention.

Figure 6:
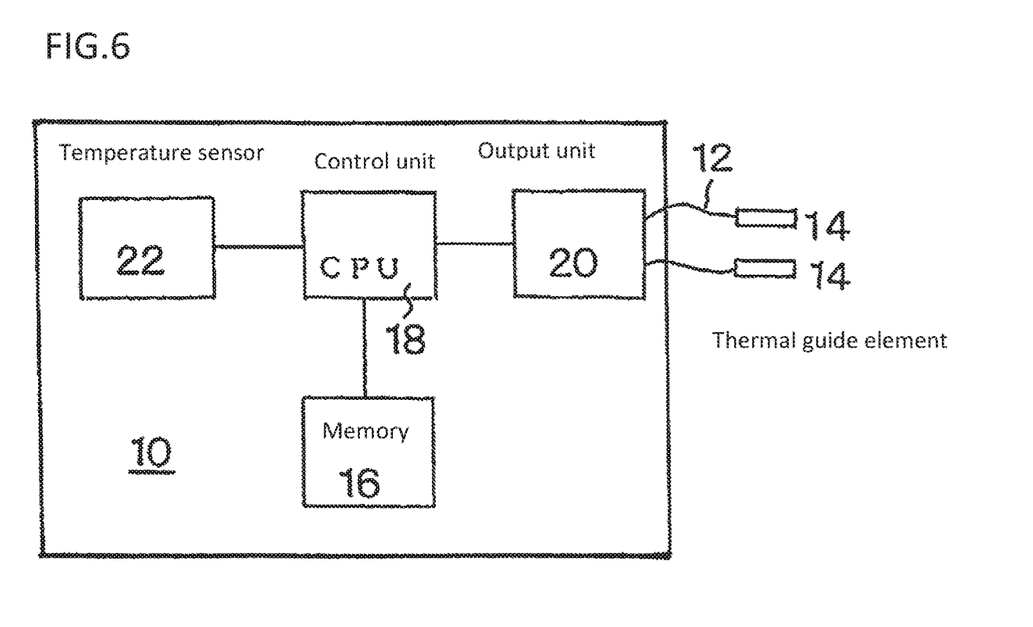
FIG. 6 is a schematic view of a circuit diagram of the electrical thermal stimulus apparatus.

FIG. 6 is a schematic view of a circuit diagram of the electrical thermal stimulus apparatus.

An electrical thermal stimulus apparatus comprises the apparatus body 10 comprising a control function, and thermal guide element 14 which is connected to the apparatus body 10 by a lead 12. As shown in FIG. 5, the apparatus body 10 comprises a memory unit 16, in which the thermal stimulus patterns are stored, a control unit (CPU) 18, which reads out a thermal stimulus pattern from the memory unit 16, and an output unit 20, which supplies the thermal stimulus pattern to the thermal stimulus guide element 14 for a thermal stimulus. A thermal stimulus is applied to a thermal stimulus applied site, according to the thermal stimulus pattern.

A control unit (CPU) 18 is connected to the memory unit 16. A thermal stimulus pattern for obtaining a stimulus condition equivalent to that obtained from combustion of moxa is stored in the memory unit 16. The control unit (CPU) 18 reads out the thermal stimulus pattern from the memory unit 16, and controls an output to a thermal stimulus guide element(s) based on detection of an temperature sensor 22, and outputs the thermal stimulus pattern to the thermal stimulus guide element(s).

The apparatus body 10 is connected to two or more thermal stimulus guide elements for a thermal stimulus in order to supply the thermal stimulus pattern to at least two different a thermal stimulus applied site. In this manner, the selected thermal stimulus pattern is applied to the thermal stimulus applied site through the thermal guide elements for thermal stimulus.

A temperature sensor 22 is provided in a position(s) which is correlated with a temperature of an affected area near the heating elements. The thermal stimulus guide elements for a thermal stimulus have a structure set forth below. The thermal stimulus guide element 14 for a thermal stimulus comprises a casing of apparatus body, a heater which is provided in the casing, and is used as a source of heating for applying thermal stimulus, a heat conduction board, which is provided on a lower face of the casing and which conducts heat of the heater to a skin of a patient, and a seal board provided on an upper face of the casing.

The thermal stimulus guide elements are provides a heat conduction board made of at least two kinds of materials. In the example, the heat conduction board use aluminum and platinum.

A temperature sensor is provided in a predetermined position of the housing which is in contact with a thermal stimulus applied site of a human body, and detects the temperature of the position, so as to send a detection signal to a sensor amplifier. The control unit (CPU) controls an output of an electric power generating circuit so that the temperature of the portion, which is in contact with a skin surface of a human body contact, may not exceed a predetermined temperature.

When the heating temperature of the thermal stimulus guide elements detected by the temperature sensor is equal to or lower than a reference temperature, a positive side period of a pulse signal is controlled so as to be long and a negative side period of the pulse signal is controlled so as to be short, according to the output of the temperature sensor. On the contrary, when it is in a state at the reference temperature, a positive side period is controlled so as to be short and a negative side period thereof is controlled so as to be long.

The method of operation in the thermal stimulus apparatus is as follows.

Figure 7:
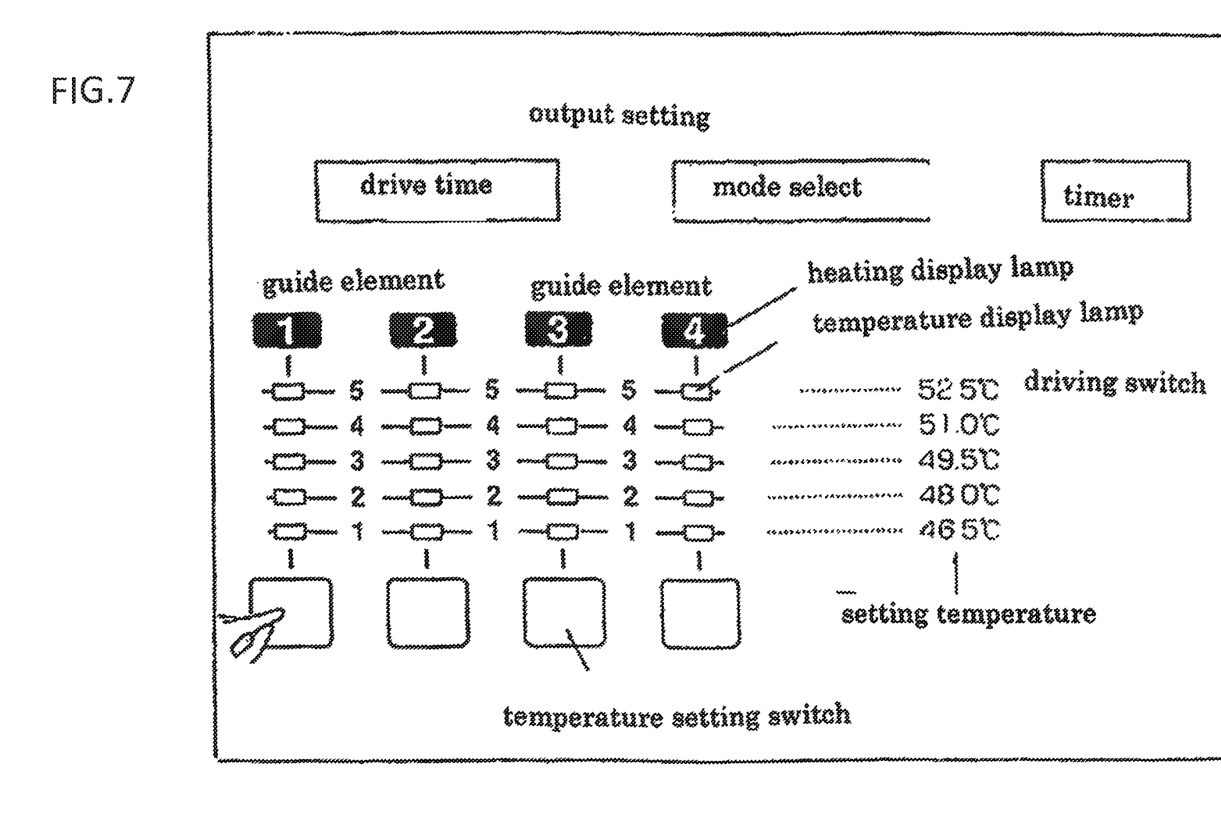
FIG. 7 is a schematic view of an arrangement of function in the electrical thermal stimulus apparatus according to the invention.

The case where the guide elements are fixed to two thermal stimulus applied sites, which are different from one another, will describe below. The guide elements are fixed to the selected thermal stimulus applied sites, and electric power is supplied from the electric thermal stimulus apparatus. Here, in temperature setting and stimulus application method of the thermal stimulus guide elements, when the number of thermal stimulus applied site is two, the thermal stimulus guide elements 1 and 2 are used (FIG. 7). The temperature is adjusted by a temperature setting switch. Every time the switch is pushed, the temperature of the elements is controlled in a range of from 46.5 to 52.5 in order of 1-2-3-4-5.

A mode selection button for selecting a warming mode, that is, an alternate mode or a sequential mode, is provided therein. In the alternate mode, heating and pausing of the two guide elements 1 and 2 are alternatively repeated. In the sequential mode, thermal stimulus of the two guide elements which are different from one another is carried out one by one in order. In this way, thermal stimulus is non-simultaneously applied to the two different sites independently of one another. The four guide elements is uses for heating (worming) the four sites. In addition, a mode of a heating interval (time) can be chosen. The alternate mode can be chosen. After, an interval mode (short, long) can be chosen. For example, in the alternate mode and short time, the guide elements 1 and 2 is heated alternately, and after five second (at time, after 10 second, also at long time, after 15 second), the heating may be stopped. In the sequential mode, the guide elements 1 and 2 is heated for 7.5 second sequentially.

Figure 8:
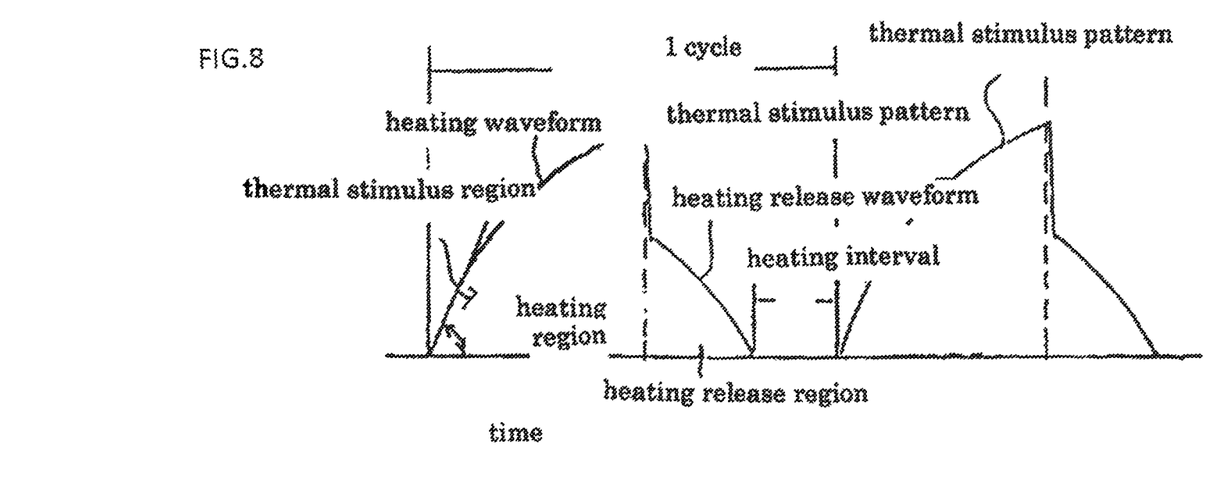
FIG. 8 shows a thermal stimulus waveform and cycle of a thermal stimulus waveform which is obtained by controlling a thermal stimulus apparatus.

FIG. 8 shows the pattern of the thermal stimulus. The pattern of the thermal stimulus is read out from the controller. The pattern read out of the thermal stimulus provides a thermal waveform 8 and an interval 7. The thermal stimulus waveform includes a heating waveform 32 obtained by heating it to a determined peak temperature, for example, 50±5 degrees Celsius, and a thermal release waveform 34 which is formed by stopping heating after it reaches the peak temperature.

The intensity of the thermal stimulus may be varying the thermal stimulus zone. The intensity of the thermal stimulus is obtained by increasing an area of the warming zone, by increasing a peak temperature, by increasing the gradient of the rising in the heating waveform, by decreasing an area of thermal release zone, by decreasing the gradient of the falling in the release waveform, by decreasing the time of interval, by increasing an time of the thermal stimulus pattern.

The thermal stimulus pattern desirably includes non-simultaneously and independent thermal stimulus waveforms whose phases are shifted so that the patterns of thermal stimulus do not substantially overlap each other at a least different two thermal stimulus applied site. The thermal stimulus is desirably a thermal stimulus.

The first thermal stimulus pattern comprises the thermal stimulus waveform configured by the heating waveform and a thermal release waveform, and an interval to the following thermal stimulus waveform in one cycle of the thermal stimulus patterns, The second thermal stimulus pattern comprises the thermal stimulus waveform for a time in the interval of first thermal stimulus pattern.

The one cycle of the thermal stimulus pattern is preferably repeated at 10 to 15 minutes. And, after the cycle of the thermal stimulus pattern is repeated at 10 to 15 minutes, and the cycle of the thermal stimulus pattern is repeated at 10 to 15 minutes.

The thermal stimulus pattern and the thermal stimulus waveform are stored in memory.

EXAMPLE

Example 1

Figure 9:
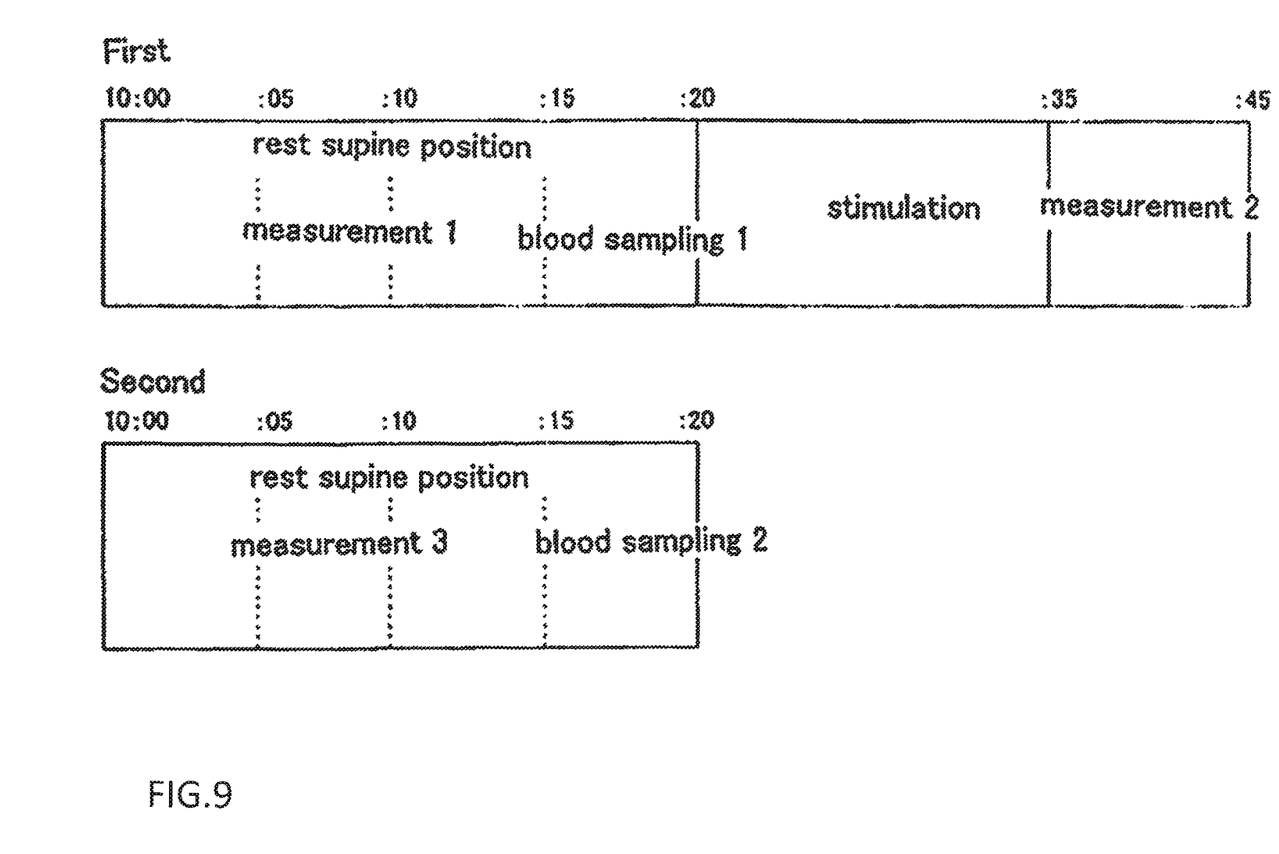
FIG. 9 is a schematic view of a thermal stimulus protocol to thermal stimulus applied sites of a body surface in foot sole of right and left.

The thermal stimulus apparatus is manufactured by BESTEC., Co. Ltd, and the thermal stimulus is carry out by using the thermal stimulus apparatus. And, the protocol of the thermal stimulus is shown in FIG. 9.

The thermal stimulus is carry out applying on thermal guide element at the specific site. The thermal guide element has a diameter; 10 mm and is set at a peak temperature; 50±5 degrees Celsius. The subjects are men and women of adult.

The thermal stimulus applied sites of a body surface preferably comprises at least one of part of os metatarsale primam 1 and 2 interosseous, part os metatarsale primam 2 and 3 interosseous, and part that intersects the perpendicular line of the medial malleolus on an extension line of the medial margin on os metatarsale primam 1 and 2 in foot sole of right and left.

The above-noted rates of increase which are previously effective on medical conditions stored in a database in FIG. 2 to FIG. 4, are recognized as effective on the following medical conditions.

1. Thermal Stimulus to Site so as to Improve Stress (Parasympathetic Nerve is Predominant) Based on Deep Body Temperature, Stress Indicator and Systolic Blood Pressure A deep body temperature increased at all the sites tested in this experiment. Among them, particularly at a site between the second and the third metatarsal heads, an increase in a temperature by 2.0625° C. is recognized after stimulus.

Salivary amylase is one indicator for evaluating stress, and it was shown that salivary amylase was likely to increase after stimulating a sole junction along a perpendicular line between the extended line between the first and second toes, and an inner ankle. Also, it was suggested that cortisol decreased at the same site.

It was recognized that systolic blood pressure decreased significantly by 13 mmHg at a site between the first and second metatarsal heads.

2. Thermal Stimulus to Site so as to Improve Liver Function

It was shown that liver functions were likely to improve by stimulating a sole junction along a perpendicular line between the extended line between the first and second toes, and an inner ankle.

3. Thermal Stimulus on Site so as to Prevent Arteriosclerosis

It was suggested that the blood pressure was decreased further (prevention of arteriosclerosis) by continuously applying thermal stimulus between the first and second metatarsal heads.

4. Thermal Stimulus to Site so as to be Effective on Diabetes

It was confirmed that glucose levels decreased by 5.00 to 5.33 between the first and second metatarsal heads and between the second and third metatarsal heads.

5. Thermal Stimulus to Site so as to Accelerate Peristaltic Motion and Absorption of Intestines It was found that the secretional capacity of gastrin as a gastrointestinal hormone accelerated significantly when stimulating a sole junction along a perpendicular line between the extended line between the first and second toes, and an inner ankle, which suggested that digestion absorption and the peristaltic motion of intestines would accelerate.

6. Thermal Stimulus to Site so as to Turn "ON" Genes of Longevity

It was shown that Adiponectin was likely to increase after stimulating a site between the first and second metatarsal heads. Adiponectin is considered as one of the substances that activate Sirtuin genes, and is one of the genes related to longevity. Thus, it is suggested that the genes related to longevity are turned ON by stimulating two locations on a sole.

7. Thermal Stimulus to Site for Dieting Effect and Obesity Prevention

Secretional capacities decreased in order of a site between the first and second metatarsal heads and a sole junction along a perpendicular line between the extended line between the first and second toes, and an inner ankle.

Example 2

A system and method for conducting a thermal stimulation treatment according to the present invention will be explained below. Any device and method disclosed above may be used to conduct the following treatments.

In accordance with a system or method for conducting a stimulus treatment of a subject or patient according to the present invention, the treatment may be conducted by using the combination of a stimulation application treatment, a dietary treatment, and a body exercise treatment so as to increase a blood flow in the subject staying in a thermal stimulation treatment institution (treatment provider or site), based on a treatment schedule prepared by the thermal stimulation treatment institution. The subject may continue to stay overnight in the institution.

The system for the stimulus treatment includes the following steps:

(1) conducting a health examination of the subject by a medical institution (any health care provider) before the subject makes her/his reservation for the stimulus treatment at the stimulation treatment institution and sending a result of the health examination to the stimulation treatment institution in which the subject is supposed to have the treatment;

(2) sending to the subject a schedule of the stimulus treatment considered to be suitable for the subject in view of the result of the health examination;

(3) making a reservation for the stimulus treatment to be performed in the stimulation treatment institution;

(4) examining the health conditions of the subject to obtain her/his examination data information after the subject starts to stay at the stimulation treatment institution and registering (storing) the examination data information in an information accumulation device;

(5) planning the schedule of the stimulus treatment, which is suitable for the subject in consideration of the examination data information obtained in the stimulation treatment institution;

(6) based on the schedule of the stimulus treatment, conducting the stimulation application treatment on the subject, i.e., applying a stimulation to a predetermined stimulation receiving site of the subject utilizing a stimulation application device (as disclosed in the present application), in which the stimulation application device is controlled so as to increase the blood flow of the subject by 60% or more after the application of stimulation, as compared to the blood flow before the application of the stimulation; and (7) in addition to the stimulation application treatment, conducting the dietary treatment and the body exercise treatment in combination with the stimulation application treatment, utilizing the blood flow as index for the treatments.

Here, the stimulation receiving site comprises at least one area selected from:

(F) site that intersects the perpendicular line of the medial malleolus on an extension line of the medial margin on os metatarsale primam 1 and 2 in foot sole;

(L) incisurasive foramen supraorbitalis site;

(K) site where the lintersection of the line connecting an augulus oculi medialis of eye and L site, and perpendicular of an augulus oculi lateralis of eye is located; and/or (M) site of augulus oculi lateralis located above 1 horizontal finger from center of the line where connect the inner end of left and right eyebrow.

More particularly, the stimulation receiving sites (L), (K), (M) and (F) are defined as follows:

(L) incisurasive foramen supraorbitalis site:
site of augulus oculi lateralis located above 1 cm from orbital height.
Site where supraorbitalis artery, vein, and supraorbitalis nerve branche at face.
Site to stimulate the blood vessel (artery) and nerve of eye;
(K) site;
Site where the lintersection of the line connecting an augulus oculi medialis of eye and (L) site, and perpendicular of an augulus oculi lateralis of eye is located.
Site where the blood flow of artery in eye amplify
Site to stimulate the peripheral nerves of eye;
(M) site;
site of augulus oculi lateralis located above 1 horizontal finger from center of the line where connect the inner end of left and right eyebrow, Site to stimulate the trochlear of eye;
(F) site (above mentioned);
Site that intersects the perpendicular line of the medial malleolus on an extension line of the medial margin on os metatarsale primam 1 and 2 in foot sole.

The blood flow is preferably measured by a laser Doppler tissue blood flowmeter mounted at the center of the inside wrist joint of the subject.

The stimulation treatment institution may obtain normal (standard or threshold) examination data information including heartbeat, irregular heartbeat, and the like (threshold values), which is associated with the decrease in the blood flow of the subject, during the stay of the subject.

The normal examination data information may be accumulated (stored) in the information accumulation device and compared with additional examination data information newly obtained from the subject. When the newly-obtained examination data information has any value outside the normal examination data information, the information accumulation device will inform the subject of the abnormality of examination data information.

When the newly-obtained examination data information is found to have any value outside the normal examination data information, the information accumulation device may send a notification to the stimulation treatment institution as well as informing the subject of the abnormality, which then allows the stimulation treatment institution to send appropriate health care advice to the subject.

The information accumulation device may be provided with an information telecommunication device which has a button with a function to send and receive the examination data information. The information accumulation device may be configured such that, when the button is one-clicked by the user, the newly-obtained examination data information is sent out to the stimulation treatment institution via the information telecommunication device.

The stimulation treatment institution may provide reward point system. Reward points may be given to the subject in accordance with the obtained increase of the blood flow such that one point may be awarded if the subject achieves 1% increase of the blood flow, for example. The subject may be rewarded with free or discount tickets or coupons for playing golf, utilizing a swimming pool, any recreation spots, restaurants, an extended stay, or a discount on treatment fees at the stimulation treatment institution based on the reward points. The stimulation treatment institution may be constructed with such affiliated facilities.

The stimulation type applied to the subject is not limited, but may be selected from thermal stimulation, electric stimulation, light stimulation, or the like. Given any type of the stimulation, the stimulation application device may preferably be adjusted and controlled, by the method discussed above in this application, so as to increase the blood flow of the stimulated site of the subject by 60% or more after the stimulation, in comparison with the blood flow before the stimulation.

In addition to the stimulation application treatment, an acupuncture treatment may preferably be performed to the subject. In addition to the stimulation application treatment, so-called "Tanden" point which is a point in a center low part of the abdomen of the subject may preferably be stimulated.

What is claimed is:

1. A method of conducting a stimulus treatment on a subject who stays at a stimulation treatment institution, based on a treatment schedule prepared by the stimulation treatment institution, the treatment comprising conducting a stimulation application treatment, a dietary treatment and a body exercise treatment in combination thereof so as to increase a blood flow in the subject, the method comprising the following steps:
   (1) subjecting the subject to a health examination by a medical institution before making a reservation for the stimulus treatment in the stimulation treatment institution and sending a result of the health examination to the stimulation treatment institution;
   (2) sending to the subject a schedule of the stimulus treatment which is considered to be suitable for the subject in consideration of the result of the health examination;
   (3) making a reservation of the stimulus treatment to be performed in the stimulation treatment institution;
   (4) examining health conditions of the subject to obtain examination data information of the subject after the subject starts to stay at the stimulation treatment institution and registering the examination data information in an information accumulation device;
   (5) planning a schedule of the stimulus treatment which is suitable for the subject in consideration of the result of the examination data information obtained in the stimulation treatment institution;
   (6) based on the schedule, conducting the stimulation application treatment by applying a stimulation to a stimulation receiving site of the subject with a stimulation application device so as to increase the blood flow in the subject by 60% or more after the application of stimulation, as compared to the blood flow before the application of the stimulation, wherein the stimulation receiving site comprises at least one area selected from the group consisting of: (F) site that intersects a perpendicular line of a medial malleolus on an extension line of a medial margin on os metatarsale primam 1 and 2 in foot sole, and (L) incisurasive foramen supraorbitalis site; (K) site where an intersection of a line connecting an augulus oculi medialis of eye and L site, and perpendicular of an augulus oculi lateralis of eye is located; and (M) site of augulus oculi lateralis located above 1 horizontal finger from center of a line where connect an inner end of left and right eyebrow; and
   (7) in addition to the stimulation application treatment, conducting the dietary treatment and the body exercise treatment in combination, utilizing the blood flow as index for the treatments.

2. The method according to claim 1, wherein the blood flow is measured by a laser Doppler tissue blood flowmeter which is mounted at a center of an inside wrist joint of the subject.

3. The method according to claim 1, which further comprise a step of obtaining normal examination data information including heartbeat or irregular heartbeat of the subject, which is associated with a decrease in the blood flow during the stay of the subject.

4. The method according to claim 3, which further comprises steps of accumulating the normal examination data information in the information accumulation device and comparing the normal examination data information with another examination data information newly obtained from the subject, the information accumulation device being configured to inform the subject of any abnormality when the another examination data information has a value outside the normal examination data information.

5. The method according to claim 4, which further comprises steps of sending a notification to the stimulation treatment institution when the information accumulation device informs the subject of the abnormality, and allowing the stimulation treatment institution to send health case advice to the subject.

6. The method according to claim 4, wherein the information accumulation device is provided with an information communication device having a button for sending and receiving the examination data information such that the another examination data information is sent out to the stimulation treatment institution via the information communication device when the button is one-clicked.

7. The method according to claim 1, which further comprises a step of giving reward points to the subject in accordance with the observed increase of the blood flow such that one reward point corresponds to 1% increase of the blood flow, wherein the subject is rewarded with tickets or coupons for playing golf, utilizing a swimming pool, a recreation spot, a restaurant, an extended stay, or a discount on treatment fees, in the stimulation treatment institution, based on the reward points.

8. The method according to claim 1, the stimulation applied to the subject is selected from the group consisting of thermal stimulation, electric stimulation, and light stimulation.

9. The method according to claim 1, which further comprises conducting an acupuncture treatment on the subject.

10. The method according to claim 1, wherein the body exercise treatment comprises an exercise which stimulates Tanden of the subject.

* * * * *